United States Patent [19]

Raffel et al.

[11] 4,089,206
[45] May 16, 1978

[54] METHOD AND APPARATUS FOR MEASURING THE PROPORTION OF UNDISSOLVED GAS IN A LIQUID COMPONENT FOR THE PRODUCTION OF FOAM MATERIALS

[75] Inventors: Reiner Raffel, Siegburg; Ferdinand Althausen, Neunkirchen; Ulrich Knipp, Schildgen-Nittum; Kurt Krippl, Monheim; Wolfgang Fohr, Neunkirchen-Salchendorf; Helmut Schwesig, Aachen, all of Germany

[73] Assignees: Maschinenfabrik Hennecke GmbH; Bayer Aktiengesellschaft, both of Leverkusen, Germany

[21] Appl. No.: 724,132

[22] Filed: Sep. 17, 1976

[30] Foreign Application Priority Data

Sep. 27, 1975 Germany .............................. 2543301

[51] Int. Cl.² .............................................. G01N 7/00
[52] U.S. Cl. .................................................. 73/19
[58] Field of Search ............... 73/19; 425/817 R, 140; 264/40.1, 40.3, 50

[56] References Cited

U.S. PATENT DOCUMENTS

| | | | |
|---|---|---|---|
| 2,138,141 | 11/1938 | Cromer | 73/19 |
| 2,141,977 | 12/1938 | Gray | 73/19 X |
| 2,280,075 | 4/1942 | Hayward | 73/19 |
| 2,668,437 | 2/1954 | Patch | 73/19 |

FOREIGN PATENT DOCUMENTS

1,359,141  7/1974  United Kingdom .................... 73/19

Primary Examiner—James J. Gill
Attorney, Agent, or Firm—Gene Harsh; Joseph C. Gil; R. Brent Olson

[57] ABSTRACT

The instant invention relates to a method and apparatus for measuring the proportion of undissolved gas in a liquid component for the production of foam materials, particularly those based on polyurethanes. The method is based on the equation of state of ideal gases (Boyle-Mariot Law: $p \cdot v = $ constant) at constant temperatures. The gaseous portion of a liquid component charged with gas increases its volume under expansion according to the above equation. The gas expansion also increases the liquid volume. The differences in the volumes, of the liquid at two differing pressures is therefore a measurement of the quantity of gas present in the liquid. The apparatus consists of a closed graduated measurement vessel being connected to a variable pressure means capable of producing at least two different defined pressures.

2 Claims, 1 Drawing Figure

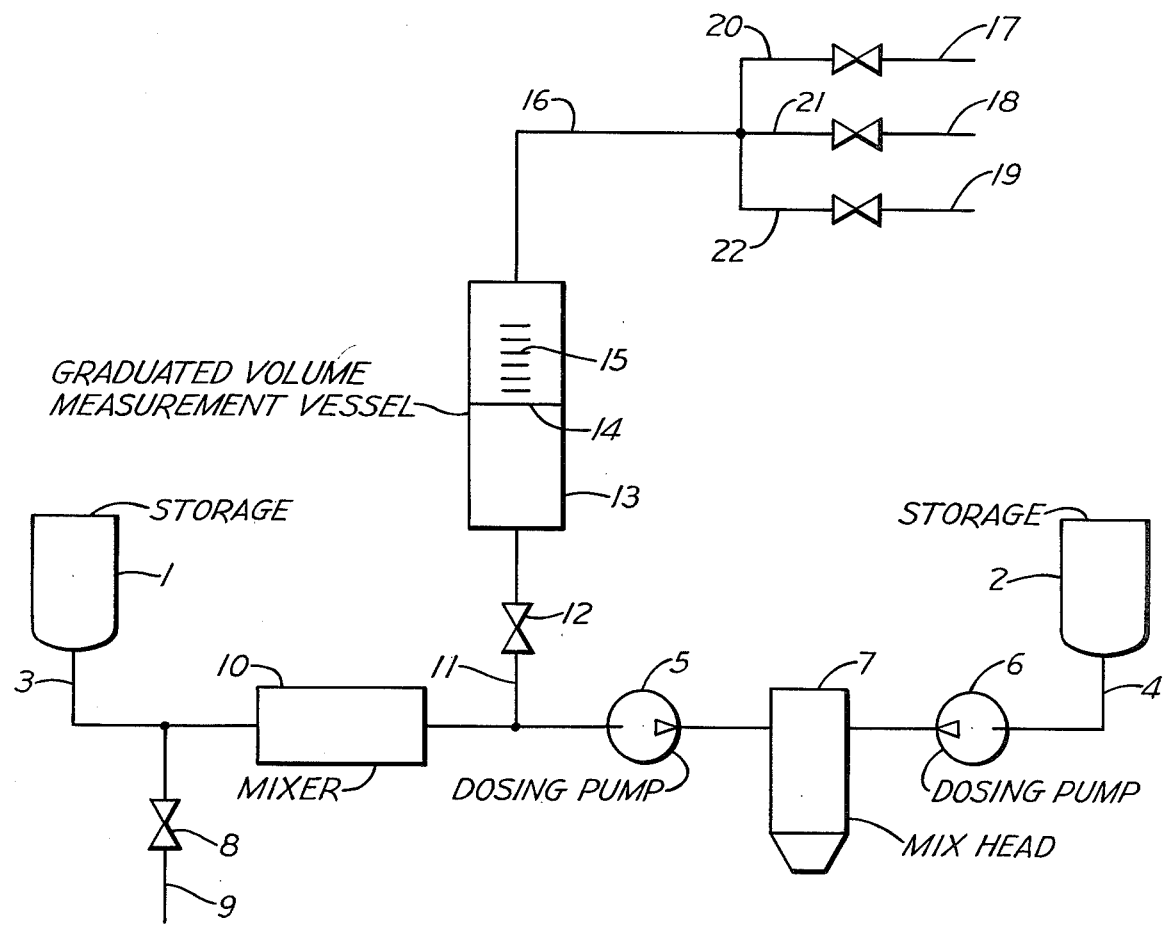

METHOD AND APPARATUS FOR MEASURING THE PROPORTION OF UNDISSOLVED GAS IN A LIQUID COMPONENT FOR THE PRODUCTION OF FOAM MATERIALS

BACKGROUND OF THE INVENTION

The present invention relates to a method and apparatus for measuring the proportion of undissolved gas in a liquid component for the production of foam materials particularly those based on polyurethane.

To induce cell formation in the foaming reaction, a specific quantity of a gas such as air, must be contained in the reaction mixture in the form of fine bubbles to serve as nuclei in the foaming reation. Depending on the various desired foam materials, a varying quantity of gas is necessary for this nucleus formation.

For this purpose, a gas such as air is introduced into one of the reaction components, which carries the gas with it into the mixing chamber, or the gas is introduced directly into the mixing chamber. The first mentioned method has been carried out in the past because during the expansion of the component charged with gas into the mixing chamber the gas is better distributed. The term "gas charge" of the reaction component is used. This is understood to mean the quantity of gas which is contained in the reaction component in the form of undissolved finely distributed gas bubbles.

The gas, such as air, may be introduced into a reaction component, preferably into the polyol component, in the case of polyurethane foamable reaction mixtures, by means of a mixing lance or by means of a fast running stirrer in the storage container. Gas may also be introduced into a reaction compound or into a premixing chamber through porous metal plates or injection nozzles via a dosing device. Finally the components are also recirculated by means of pumps and the return flow is fed into the gas chamber of the storage container which is under supply pressure, whereby gas is absorbed.

All these methods are extremely inaccurate and uncertain and hitherto have been conducted purely according to trial and error. In previous methods therefore, control of the gas was very unstable. The only control was the visual evaluation of the finished product. If, in the case of structural hard polyurethane foam material, the color was dark brown, then it contained too little gas. If the color was light brown, the gas proportions were correctly selected. If the foam was light brown with surface bubbles, then the foam contained too much gas.

The object of the present invention is therefore to provide a method and apparatus with which gas charges are measurable, i.e. measurable in such a way as to be reproducible.

BRIEF DESCRIPTION OF THE DRAWING

An embodiment of the apparatus according to the invention is shown in the drawing.

DESCRIPTION OF THE INVENTION

According to the invention, there is provided a method for measuring the proportion of undissolved gas in a liquid component for the production of foam materials, in particular those based on polyurethane, comprising introducing a defined quantity of a liquid component containing a gas at a first defined pressure into a graduated volume measurement vessel, changing the pressure in the vessel to a second defined pressure and measuring the resulting change in the volume of the liquid containing the gas, whereby the proportion of undissolved gas in the liquid component may be determined.

The method is based on the equation of state of ideal gases (Boyle-Mariot Law: $p \cdot v =$ constant) at constant temperatures. For example, the gaseous portion of a polyol charged with gas increases in volume by expansion according to the above equation. The gas expansion thereby causes expansion of the polyol gas mixture. Consequently, the volume of a polyol-gas mixture at 1 bar is greater than the volume of the mixture at 100 bars. The difference between the volumes of the polyol-gas mixture before and after expansion is therefore a measurement of the quantity of gas present in the polyol.

In order to assess the correct gas charge, a characteristic volume difference must be determined for each mixture system, for which the finished foam material product exhibits the desired optimum optical and mechanical characteristics. This empirically determined value for the volume difference of the gas charged component then serves as an ideal value for the correction of the gas charge either manually or automatically.

According to the invention there is also provided an apparatus for carrying out the method, comprising (1) storage containers for liquid components, from which input conduits lead via dosing pumps to a mixing head, (2) a gas inlet conduit connected to at least one of the input conduits of the components and (3) a closeable branch conduit connected at one end to the input conduit between the gas inlet conduit and the mixing head and at the other end to an inlet for a closed graduated measurement vessel which is connected to a variable pressure means capable of producing at least two different defined pressures.

The variable pressure means is used to apply different pressures to the mixture in order to ascertain the change in volume of the quantity of the mixture which is in the closed graduated measurement vessel, at the differing pressures. Of course, the variable pressure means can be constructed in many different ways. Preferably it should consist of a gas pipe which can be closed and which opens out into the volume measurement vessel, the gas pipe being connected to a source of pressurized gas. This embodiment ensures particularly simple handling of the measuring part of the apparatus. In principle this variable pressure means can also be designed to operate mechanically or hydraulically.

One embodiment of the method according to the invention provides not only for the measurement of the gas charge, but also for its regulation. The measuring process can be automated, by removing a sample at periodic intervals by means of a conventional device, measuring the gas charge and regulating the flow of gas in the gas inlet conduit to reduce the difference between the measured value of the gas charge. If the measured value agrees with the ideal value, then of course no correction is required.

An embodiment of the apparatus according to the invention is shown in the drawing and illustrated further below.

Pipes 3, 4 lead from storage containers 1, 2 via dosing pumps 5, 6 to a mixing head 7. A gas inlet pipe 9 provided with a throttle valve 8 opens into the pipe 3. Downstream of the gas inlet pipe 9 is arranged a through-run mixer 10 in pipe 3. A branch pipe 11, in which a stop valve 12 is arranged, leads from pipe 3 to a graduated volume measurement vessel 13. The vessel 13 is marked with a filling mark 14 and a measuring scale 15. In addition, a gas pipe 16 opens into the volume measurement vessel 13, and the gas pipe 16 is connected to branch pipes 20, 21, 22 respectively provided with stop valves 17, 18, 19.

The method of operation is as follows:

The polyol and isocyanate components are pumped from the storage containers 1, 2 by dosing pumps 5, 6 through pipes 3, 4 to the mixing head 7, where they are mixed and the mixture ready for reaction is discharged. Through gas inlet pipe 9, a corresponding quantity of air, adjusted by throttle valve 8 is continuously introduced into the polyol and finely distributed by means of the mixer 10. The stop valves 18 and 19 are closed. Stop valve 12 of branch pipe 11 is periodically opened, in order to remove a defined volume of the mixture of air and polyol. For this purpose the stop valve 17 in the branch pipe 20 is opened, whereby a pressure of, for example, 3 bars is applied, which is lower than the pumping pressure of the polyol of 4 bars. When the mixture flowing has reached the filling mark 14, the stop valves 12 and 17 are closed. Then the stop valve 18 is opened and the pressure in the inner chamber of the volume measurement vessel 13 is reduced to, for example, 0.5 bars. The volume of the mixture then increases. The differential value indicated is a measurement of the gas charge. Then the stop valve 12 is opened, so that the sample can flow back into the pipe 3. However, the stop valve 19 must be opened and air must be introduced into the volume measurement vessel 13 through the gas pipe 16, which is under a higher pressure e.g. 5 bars, than the pumping pressure of the polyol (4 bars). If the stop valve 19 is closed again the next measurement procedure can begin.

Of course the measurement can be automated, by controlling the throttle valve 8 by means of suitable control units as a function of the volume differential value displayed so that the ideal value of the gas charge is maintained.

The present invention is particularly adapted for use in the production of polyurethane foams. As is well known in the art and foams are generally produced by reacting organic isocyanates, and active-hydrogen containing materials in the presence of blowing agents. Preferred active-hydrogen materials are hydroxyl containing materials such as polyether polyols, polyester polyols and the like. As is known in the art, these foams are produced by mixing two or more streams, one stream containing the isocyanate and one stream containing the active hydrogen containing materials.

What is claimed is:

1. An apparatus for measuring the proportion of undissolved gas in a liquid component for foam materials comprising (1) a storage container for said liquid component, from which an input conduit leads via a dosing pump to a mixing head, (2) a gas inlet conduit connected to said input conduit, and (3) a closeable branch conduit connected at one end to the input conduit between the gas inlet conduit and the mixing head and at the other end to an inlet for a closed graduated measurement vessel, which is connected to a variable gas pressure means capable of producing at least two different defined pressures.

2. An apparatus according to claim 1, wherein the variable gas pressure means comprises a conduit which is connectable to at least two sources of gas at different defined pressure.

* * * * *